US006268204B1

(12) United States Patent
Miller et al.

(10) Patent No.: US 6,268,204 B1
(45) Date of Patent: Jul. 31, 2001

(54) METHOD AND DEVICE FOR BIOREMEDIATION

(75) Inventors: Donald James Miller, Verona; Susanne Selman, Madison, both of WI (US)

(73) Assignee: Promega Corporation, Madison, WI (US)

( * ) Notice: Subject to any disclaimer, the term of this patent is extended or adjusted under 35 U.S.C. 154(b) by 0 days.

(21) Appl. No.: 08/265,698

(22) Filed: Jun. 24, 1994

Related U.S. Application Data (63) Continuation of application No. 07/869,797, filed on Apr. 16, 1992, now abandoned.

(51) Int. Cl.[7] .................................. B09B 3/00; C02F 3/00
(52) U.S. Cl. ........................................ 435/262.5; 210/606
(58) Field of Search .............................. 435/262, 262.5, 435/131, 136, 171, 192; 210/606

(56) References Cited

U.S. PATENT DOCUMENTS

| 4,554,075 | 11/1985 | Chang et al. | 435/262 |
|---|---|---|---|
| 4,655,926 | 4/1987 | Chang et al. | 435/262 |
| 4,687,741 | 8/1987 | Farrell et al. | 435/262 |
| 4,687,745 | 8/1987 | Farrell | 435/262 |
| 4,690,895 | 9/1987 | Farrell | 435/262 |
| 4,891,320 | 1/1990 | Aust et al. | 435/262 |

FOREIGN PATENT DOCUMENTS 0 406 617 A2   9/1991   (EP) .

OTHER PUBLICATIONS

Bailey et al. Biochemical Engineering Fundamentals, 2nd Edition, Mcgraw–Hill Book Co., New York, (1986), p. 767.*
Biosis Abstract 86:126779 Glenn et al.*
Glenn et al., Arch. Biochem, Biophys. 251:688 (1986).
Lackner et al., Biochem. Biophys. Res. Comm. 178:1092 (1991).
Mileski et al, Appl. Environ. Microbiol. 54:2885 (1990).
Dosoretz et al., Appl. Environ. Microbiol. 56:3429 (1990).
Lin et al., Biotech. Bioengineering 35:1125 (1990).
Tien and Kirk, Methods Enzymol. 161:238 (1988).
Eaton,, Enzyme Microbiol. Techniques 7:104 (1985).
Bumpus et al., Science 228:1434 (1985).
Valli and Gold, J. Bacteriol. 173:345 (1991).
Hammel and Tardone, Biochem. 27:6563 (1988).
Kennedy et al., Appl. Environ. Microbiol. 56:2347 (1990).
Wariishi et al., Biochem. Biophys. Res. Comm. 176:269 (1991).
Kuwahara et al. FEBS 169:1383 (1984).
Lamar et al., Appl. Environ. Microbiol. 56:3519 (1990).
Lamar and Dietrich, Appl. Environ. Microbiol. 56:3093 (1990).
Bumpus and Brock, Appl. Environ. Microbiol. 54:1143 (1988).
Hammel et al., J. Biol. Chem. 261:16948 (1986).
Bumpus and Aust., Appl. Environ. Microbiol. 53:2001 (1987).
Aitken et al., Water Res. 23:443 (1989).
Wariishi et al., Biochem. 28:6017 (1989).
Michel et al., Appl. Environ. Microbiol. 57:2368 (1991).
Venkatadri and Irvine, Appl. Environ. Microbiol. 56:2684 (1990).
Fernando et al., Appl. Environ. Microbiol. 56:1666 (1990).
Bumpus, Appl. Environ. Microbiol. 55:154 (1989).
Arjmand and Sandermann, Z. Naturforsch 41c:206 (1986).
Perie and Gold, Appl. Environ. Microbiol. 57:2240 (1991).
Karhunen et al., Arch. Biochem. Biophys. 279:25 (1990).
Forrester et al., Appl. Microbiol. Biotechnol. 33:359 (1990).
Johansson and Nyman, Acta Chemica Scand. B41:762 (1987).
Nerud and Miscurcova, Biotechnol. Letters 11:427 (1989).
Galliano et al., Enzyme Microbiol. Technol. 13:478 (1991).
Popp and Kirk, Arch. Biochem. Biophys. 288:145 (1991).
Jager and Wandrey, in Physiology of Immobilized Cells, pp. 433–438 (J.A.M. de Bont et al., eds) (Elsevier, Amsterdam, 1989).
Brown et al., J. Bacteriol. 172:3125 (1990).
Forrester et al., Biochem. Biophys. Res. Comm. 157:992 (1988).
K. Polvinen et al., Chapter 18, In: ACS Symposium Series, vol. 460, G.F. Leatham and M.E. Himmel eds. (American Chemical Society 1991).

* cited by examiner

*Primary Examiner*—Curtis E. Sherrer
(74) *Attorney, Agent, or Firm*—Medlen & Carroll, LLP (57) ABSTRACT

The degradation of compounds contained in a liquid or solid waste stream is described. The invention provides a system that can be operated economically on a commercial scale that is capable of handling diverse waste streams without significant inhibition of the degradation process. The system involves the use of a semi-permeable membrane partition and pressure to drive reactants into a waste stream.

25 Claims, 7 Drawing Sheets

METHOD AND DEVICE FOR BIOREMEDIATION

This is a Continuation of copending application Ser. No. 07/869,797 filed on Apr. 16, 1992.

FIELD OF THE INVENTION

This invention relates to biological treatment of waste, and particularly to the degradation of organo-halides contained in liquid wastes.

BACKGROUND

Industrial processes that use or generate toxic organic compounds has lead to the contamination of nearby water and land. Most approaches to decontamination or "remediation" involve stopping the local dumping of such compounds and transport of the waste to another area for containment. This is costly and does not eliminate the hazard.

As a remediation technology, bioremediation is considerably more attractive. Rather than merely transporting wastes, it offers the possibility of degrading toxic compounds to harmless reaction products by the use of biologicals.

Bioremediation field trials have involved both in-situ and ex-situ treatment methods. Typically, ex-situ treatment involves the transfer of contaminated waste from the site into a treatment tank designed to support microbial growth, i.e., a "bioreactor". The reactor provides for effective mixing of nutrients and control over temperature, pH and aeration to allow optimum microbial growth.

In-situ treatment involves adding biologicals directly to the waste. This avoids the problems associated with handling (e.g., pumping) toxic compounds. However, in-situ treatment has its own problems. Unlike bioreactors, where microbial growth can be monitored and adjusted, in-situ environmental conditions are difficult to measure and control.

Bioremediation technologies being developed to deal with waste differ further in their ability to handle specific types of compounds. For example, the effluents from most pulp or paper-making operations contain lignin or its degradation products. Lignin is an extremely complex polymer, constituting up to 35% of dry wood weight. During pulping processes, cellulose fibers must be liberated from the surrounding lignin matrix so that they can be associated with one another. The resulting free lignin is highly resistant to degradation.

Chang et al. describe the degradation of the complex lignin polymer by direct addition of cultures of the white-rot fungus, *P. chrysosporium*. See U.S. Pat. No. 4,655,926, hereby incorporated by reference. They describe the induction of lignin degradation in response to carbon and nitrogen starvation.

This fungal lignin metabolism is a secondary metabolic event. Lignin degradation allows the fungus to expose the cellulose contained within the lignin matrix as its primary food source. Indeed, lignin alone will not support *P. chrysosporium* growth.

Since cellulose fibers are the primary food source, degradation of lignin by adding the fungus directly to the wood results in reduced pulp yield and an inferior pulp product. Farrell has proposed, therefore, an improvement in lignin degradation. See U.S. Pat. Nos. 4,687,745 and 4,690,895, hereby incorporated by reference. She describes the use of fungal enzymes rather than fungal cultures. The enzymes degrade lignin without degrading cellulose fibers.

The mechanism by which these enzymes degrade lignin has been investigated. Glenn et al. have characterized the enzyme manganese peroxidase. See Arch. Biochem. Biophys. 251:688 (1986). By separating the enzyme from the substrate using a membrane, they showed that Mn(III) complexed to lactate or other hydroxy acids are intermediates capable of oxidizing organic compounds. This work was confirmed by Lackner et al., Biochem. Biophys. Res. Comm. 178:1092 (1991).

Lignin is but one by-product of paper making operations. The bleaching of paper with chlorine generates effluents that are a serious health concern. Many of these compounds are known to cause cancer in humans. Most importantly, these compounds are not degraded rapidly in the natural environment.

Chang et al. teaches that chloro-organics contained in liquid waste can also be degraded by the white-rot fungus. See U.S. Pat. No. 4,554,075, hereby incorporated by reference. In the method proposed, the fungus is immersed in the liquid containing chloro-organics and periodically exposed to an oxygen enriched atmosphere. The chloro-organics are converted from aromatics to aliphatics.

Unfortunately, the rate of chloro-organic degradation is slow since the degradation activity must be induced by starvation of the organism. To avoid the necessity for this starvation step, Aust et al. teach the direct addition of fungal enzymes rather than whole organisms. See U.S. Pat. No. 4,891,320, hereby incorporated by reference. They suggest the direct addition of a fungal peroxidase. This, however, requires the continually mixing of the enzyme with hydrogen peroxide. This is difficult whether done in an open environment or a closed reactor.

Indeed, the commercial use of fungal degradation is hampered by complex technical and engineering issues. Growth of the organism and/or enzyme production may be inhibited by waste components. See generally, Mileski et al., Appl. Environ. Microbiol. 54:2885 (1988). Furthermore, the enzyme is a protein and, as such, can undergo proteolysis by any number of proteases in the waste stream, and be rendered thereby inactive. See Dosoretz et al., Appl. Environ. Microbiol. 56:3429 (1990). In sum, the degrading ability of *P. chrysosporium* is not practically maintained for a very long period of time. See Lin et al., Biotechnology and Bioengineering 35:1125 (1990).

There remains a need to develop a bioremediation procedure that can be operated economically on a commercial scale. Such a procedure must be able to deal with diverse waste streams without significant inhibition of the degradation process.

SUMMARY OF THE INVENTION

This invention relates to biological treatment of waste, and particularly to the degradation of organo-halides contained in liquid wastes. In one embodiment, the present invention contemplates a method of degrading compounds contained in a liquid or solid waste stream, comprising the steps of: a) providing, i) a reaction containing means having a semi-permeable membrane partition, ii) at least one enzyme for which the membrane is not permeable, and iii) at least one substrate for the enzyme; b) adding to the containing means on one side of the partition, the enzyme and substrate to create a reaction mixture, thereby generating a reaction intermediate for which the membrane is permeable; c) adding to the containing means on the other side of the partition, the compounds contained in said waste stream, d) applying a pressure to the reaction mixture so as to force the reaction intermediate across said membrane into the compound-containing waste stream, thereby degrading the compounds.

In another embodiment, the present invention contemplates a method of degrading compounds contained in a liquid or solid waste stream, comprising the steps of: a) providing, i) a first reaction containing means having a semi-permeable membrane partition, ii) at least one enzyme for which the membrane is not permeable, and iii) at least one substrate for the enzyme, and iv) a second reaction containing means; b) adding to the first containing means on one side of the partition, the enzyme and substrate to create a reaction mixture, thereby generating a reaction intermediate for which the membrane is permeable; c) applying a pressure to the reaction mixture so as to force the reaction intermediate across said membrane and so as to collect the reaction intermediate on the other side of the partition; and, d) adding the reaction intermediate to the second containing means wherein the compounds to be degraded are contained, thereby degrading the compounds. In one embodiment, the reaction intermediate is added in step (d) by pumping the intermediate from the first reaction containing means to the second reaction containing means.

In one embodiment said enzyme is derived from white-rot fungus. In one embodiment, the fungus is selected from the group comprising *Phanerochaete chrysosporium, Dichromitus squalens, Phlebia radiata, Lentinula edodes, Trametes versicolor, Coriolopsis occidentalis, and Rigidoporus lignosus*.

It is preferred that the enzyme is a peroxidase. In one embodiment, the substrate is Mn(II). It is preferred that Mn(II) is added in the presence of an α-hydroxy acid and $H_2O_2$. In such a case the reaction intermediate is a Mn(III)-α-hydroxy acid complex. In one embodiment, the α-hydroxy acid is selected from the group comprising lactic, malonic, malic, oxalic, pyruvic and tartaric acid.

It is not intended that the present invention be limited to the compounds exemplified below. The compounds to be degraded may be selected from the group comprising olefins, diols, organic acids, halogenated and non-halogenated aromatics and polyaromatics, dyes and lignin, including halogenated lignin such as chlorolignin. Halogenated aromatics of particular importance are the chlorinated aromatics, including but not limited to pentachlorophenol, trichlorophenol, and dichlorophenol. Important dyes decolorized by peroxidase include crystal violet, bromothylmol blue, methyl green, arsenazo, phenol red, methylene blue, brilliant blue G, brilliant blue R, thymol blue and ethidium bromide. A representative hydroxy ketone is cyclohexanone. Other compounds of some importance in waste include toluene and formaldehyde.

The present invention is also useful for decolorization of waste. In particular, the method of the present invention is useful for the decolorization of paper mill effluent and waste containing dyes.

DESCRIPTION OF THE INVENTION

This invention relates to biological treatment of waste, and particularly to the degradation of organo-halides contained in liquid wastes. The present invention contemplates both a method and device for degrading a diverse group of compounds contained in a solid or liquid (e.g., paper pulp, pulp mill effluent, sludge, wastewater, etc.).

Figure 1:
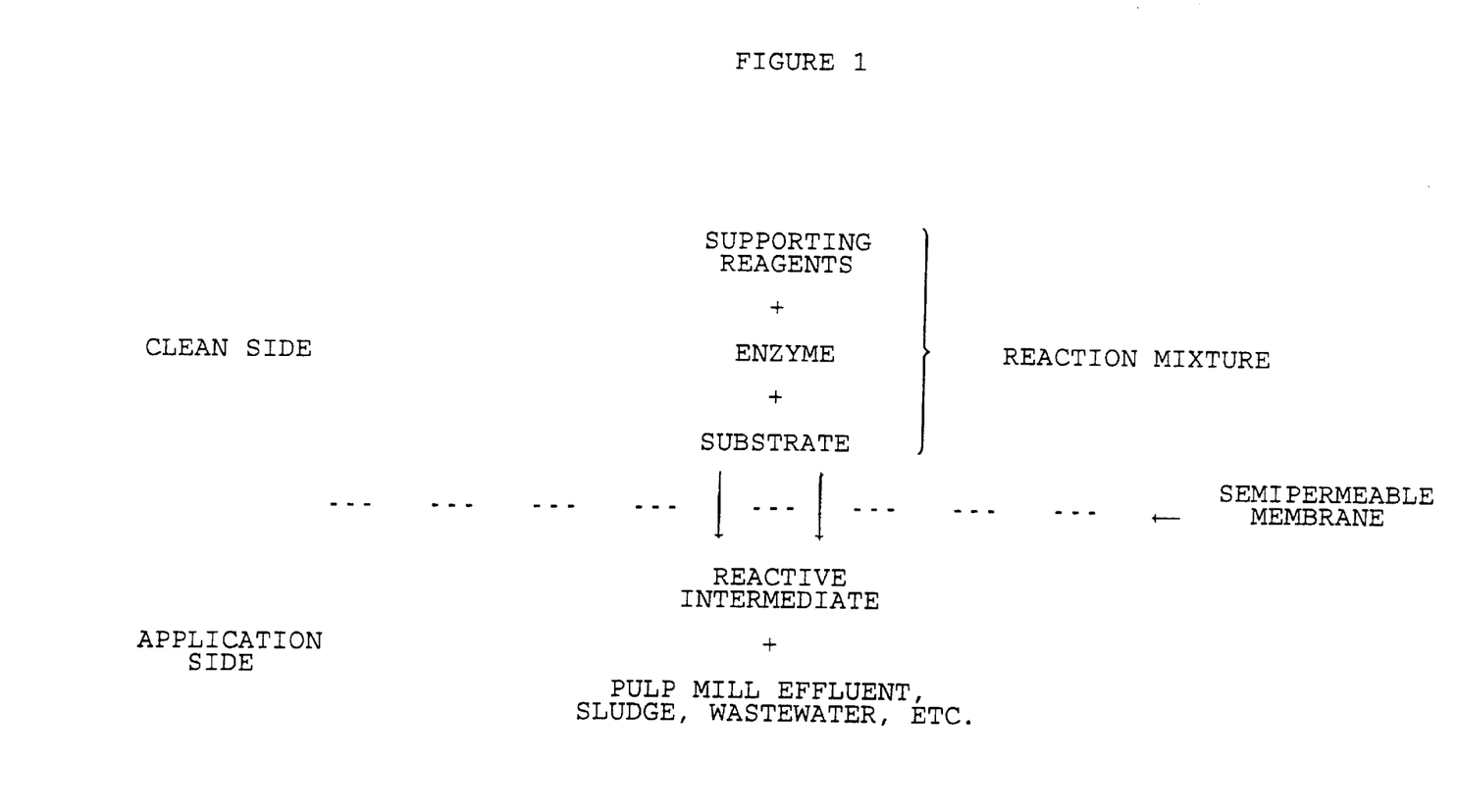
FIG. 1 schematically shows the membrane feature of the present invention.

The invention employs enzymes in combination with a semi-permeable membrane system in a reaction containing means, such that the enzyme, substrate and supporting reagents are separated by a partition from the compounds to be degraded (see FIG. 1). It is contemplated that an enzyme, incapable of passing through the membrane, will undergo a reaction with a substrate on the "clean side" of the partition so as to generate a reactive intermediate capable of passing through the semi-permeable membrane to the "application side" of the partition into the compound-containing liquid or "application stream", thereby degrading the compounds.

Unlike prior approaches, the approach of the present invention allows the enzyme to remain localized in an environment where it is stable and productive for much longer periods of time. In this configuration, the enzyme is not inhibited by waste components. Consequently, far less of the enzyme is consumed, yielding a major savings. Further, the concentrations of the different reagents in the reaction mixture can be monitored and controlled more easily to achieve optimal concentrations and conditions (e.g., pH) to generate the best rates and yields.

While the present invention contemplates that the reactive intermediate may passively travel through the membrane, this approach is inefficient. Indeed, in large scale systems, passive transfer is very slow and largely ineffective. It is preferred, therefore, that the intermediate be subjected to a force to drive it across the membrane. In one embodiment, the present invention contemplates applying a pressure to the reaction mixture so as to force the reaction intermediate across the membrane.

There are significant advantages to using a force to drive the intermediate. First, since the mass flux is toward the application stream, there is little or no fouling of the membranes for long periods of time since oils and particulates are continuously swept from the application side of the membrane by the pressure differential. To further exploit this advantage, a counter-current mass transfer may be achieved, if the nature of the application stream allows, by pumping the material to be treated in the opposite direction of the intermediate generating stream, thus exploiting pressure and concentration differences between both streams to the fullest advantage. In the event of high viscosity, chemical incompatibilities or large particulates in the application stream, the flux may be collected from the filtration device and introduced to the stream separately upstream from static or agitated mixing.

DESCRIPTION OF EMBODIMENTS OF THE INVENTION

Figure 2:
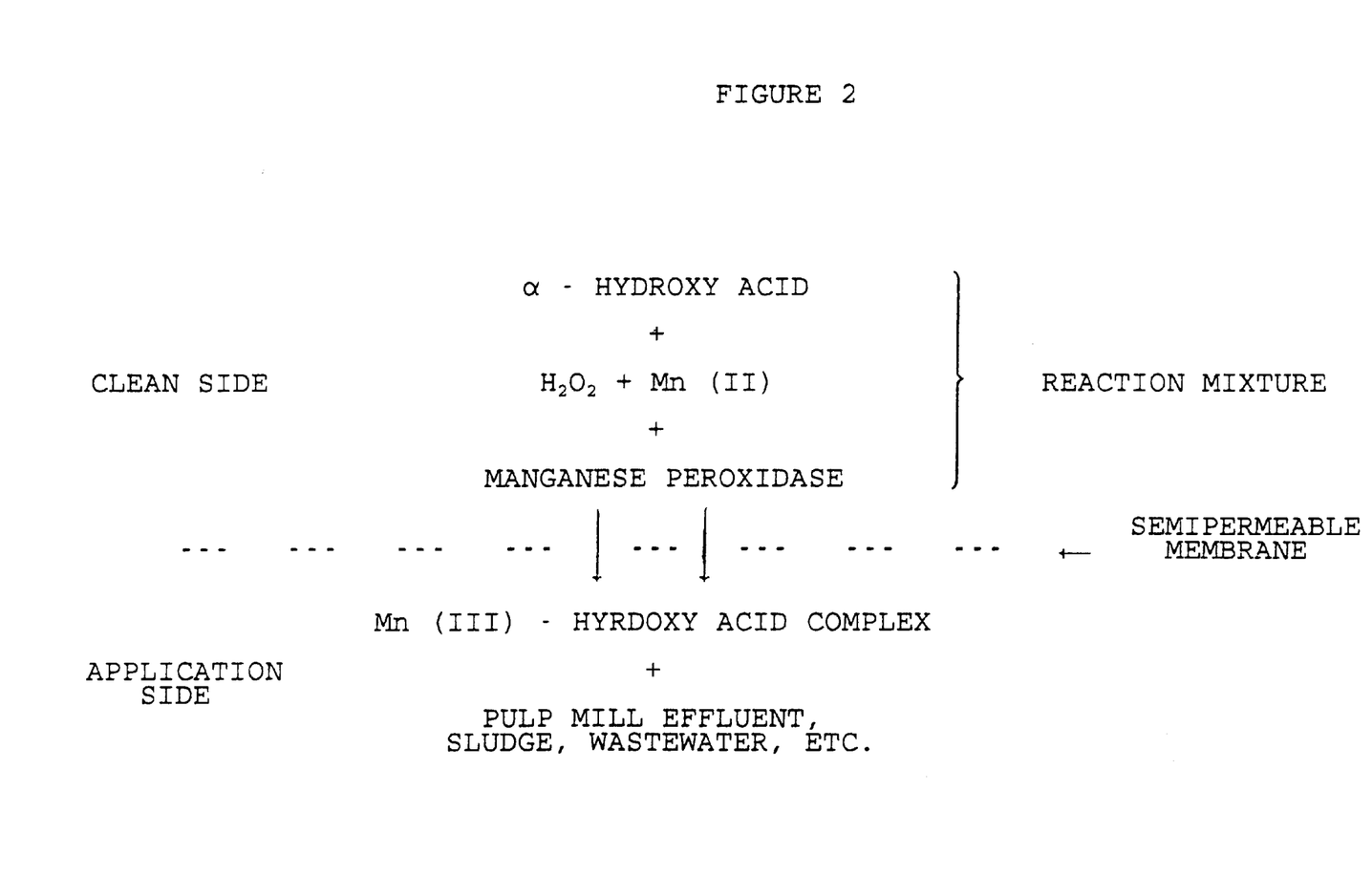
FIG. 2 schematically shows the membrane feature of the present invention in the context of a preferred enzyme for degradation.

In one embodiment the enzyme used is derived from the white-rot fungus *P. chrysosporium*. It is preferred that the enzyme is a peroxidase such as a manganese peroxidase. In one embodiment, the substrate is Mn(II) that is added in the presence of an α-hydroxy acid and hydrogen peroxide. In such a case the reaction intermediate is a Mn(III)-α-hydroxy acid complex (see FIG. 2). Where lactic acid is employed, the intermediate is a Mn(III)-lactate complex.

A semi-permeable membrane provides a practical method of keeping the Manganese (III) generating system separate from the application matrix while allowing the Mn(III) complex to reach the eventual point of use. In one embodiment, this is accomplished by performing the reaction on the high pressure side of a membrane device and allowing the Mn(III) complex to flux through the membrane and into the application stream. Importantly, the membrane is sized so as to retain the enzyme while allowing the Manganese (III) complex to pass into the application stream. The conditions of the reaction involving the enzyme are monitored and controlled. The optimal pH is 5.0 for enzymatic Mn (III) production. This is in contrast to the optimal pH (pH 2.5–3.0) for Mn(III) oxidation of compounds in the application stream.

This embodiment is adaptable to any application where aqueous Mn(III) complexes are useful for degradation of compounds and particularly organo-halides contained in liquid wastes. This approach to bioremediation represents a significant advance over the current state of the art.

Figure 3:
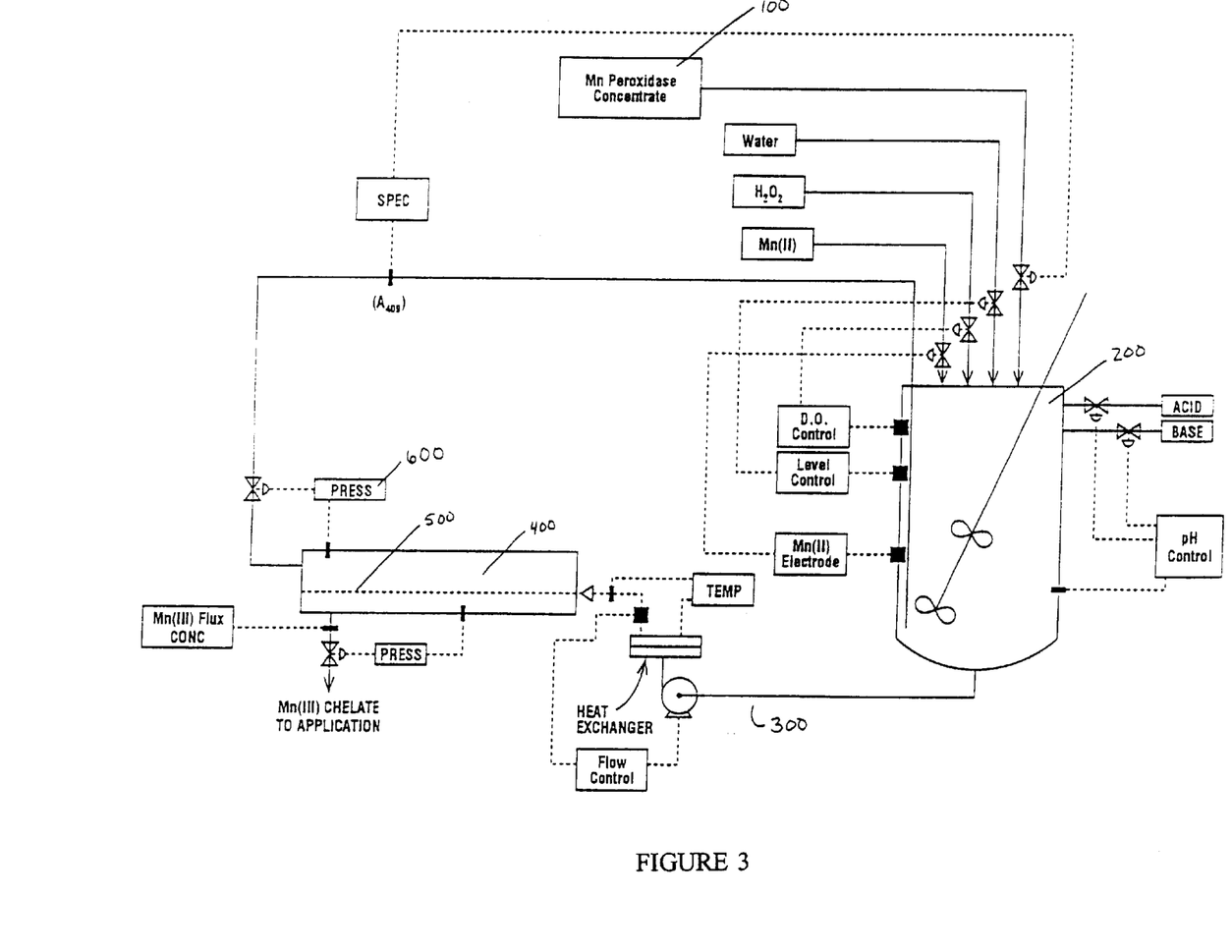
FIG. 3 is an instrumentation diagram schematically showing one embodiment of the device of the present invention in the context of a preferred enzyme for degradation.

FIG. 3 schematically shows one embodiment of the device of the present invention. In this embodiment, manganese peroxidase derived from white-rot fungus is provided via providing means (100), along with other reagents (water, hydrogen peroxide and Mn(II) substrate), to a reaction containing means or reservoir (200) to create a reaction mixture, thereby generating a reaction intermediate. The reservoir (200) is connected via a flowing means (300) to a chamber (400) having a semi-permeable membrane partition (500). The membrane (500) is not permeable to the peroxidase but is permeable to the reaction intermediate Mn(III). A pressure is applied to one side of the membrane via a pressure applying means (600) so as to force the reaction intermediate across the membrane. At this point the reaction intermediate can be collected and added to a second containing means wherein the compounds to be degraded are contained, thereby degrading the compounds. In one embodiment, the reaction intermediate is added by pumping the intermediate from the first reaction containing means to the second reaction containing means. The enzyme can then be recirculated back from the chamber (400) to the reservoir (200) via the flowing means (300) for further reactions.

The reaction mixture is monitored and controlled to provide the best possible Mn(III) production rate per unit volume, factoring in allowances for enzyme stability, Mn(II) to Mn(III) conversion efficiencies, and flux of non-converted reactants. The soluble enzyme remains stable and active for many hours of continuous operation. A typical reaction occurs at 20° C. (there can be an in-line heat exchanger for temperature adjustments) at pH 4.5–5.5 under controlled conditions, with constant feeding of hydrogen peroxide, an α-hydroxy acid, and Mn(II). This generates a yield of Mn(III) of approximately 5–10 mM/hr/mg enzyme or 300–500 mg/hr/mg enzyme.

The bioremediation system of the present invention need not be large. A protein concentration of 1.0–2.0 mg per liter in a reservoir (200) of ten liters, connected to a chamber (400) with a holdup volume of five liters having a membrane (500) of twenty-five square feet of surface area is capable of generating enough reaction intermediate to process 750–10,000 liters per hour of contaminated water.

The volume of the reservoir (200), and consequently the recirculation and reactant volumes, should be kept to a minimum to maintain the enzyme concentration as high as possible for purposes of stability and complete conversion. On the high pressure side of the membrane (500), there should be monitoring and/or control elements for a) enzyme, peroxide and Mn(II) concentrations, b) pH, c) flow rate, and d) transmembrane pressure differential. On the low pressure side of the membrane (500), there should be monitoring and/or control elements for a) Mn(III) concentration, and b) flux rate. The entire system can be placed conveniently under the control of individual loops or cascaded into a local batch controller or minicomputer for more exacting applications.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade).

Unless otherwise indicated, enzyme was obtained from *P. chrysosporium* strain BKM-F-1767 (ATCC #24725) which was maintained and grown essentially according to Tien & Kirk Meth. Enz. 161:238 (1988). Production of spores was done in tissue culture flasks (Corning 25160-225) containing 100 ml of the following (per L) 10 g glucose; 10 g malt extract; 2 g peptone; 2 g yeast extract; 1 g asparagine; 2 g $KH_2PO_4$; 1 g $MgSO_4.7H_2O$; 1 mg thiamine.HCl; 20 g agar. After three days to several weeks, the spores are washed out with sterile water and kept at 4° C. until use.

Growth conditions can be selected to either produce predominantly Lignin peroxidase or Manganese peroxidase, respectively, by varying the $MnSO_4$ concentration. In both cases, the fungus was grown under nitrogen-limiting conditions to induce secondary metabolism. The growth media is shown in Table 1. The list of trace elements is shown in Table 2.

TABLE 1

GROWTH MEDIA (PER LITER)

| Amount | Component |
|---|---|
| 10 g | glucose |
| 0.2 g | diammonium tartrate as nitrogen source |
| 10 mM | dimethylsuccinate (pH 4.5) |
| 2 g | $KH_2PO_4$ |
| 0.5 g | $MgSO_4.7H_2O$ |
| 0.1 g | $CaCl_2.2H_2O$ |
| 1 mg | thiamine HCl |
| 0.5 g | Tween 80 |
| 5 g | veratryl alcohol |
| 50 ml | trace elements |

$MnSO_4$ concentration was either 10 ppm (180 $\mu$M) for predominant Lignin peroxidase production or 40 ppm (740 $\mu$M) for exclusive Manganese peroxidase production.

The cultures were inoculated with $5\times10^5$ spores/ml either in 2.8 L Fernbach flasks with 1 L medium or in a 15 L stirred tank (New Brunswick FS 314 with F-14 100 tanks) with 12 L medium.

After two days of growth, veratryl alcohol and $MnSO_4$ was added and the cultures were flushed (1 L) or sparged (12 L) with pure oxygen twice daily. Manganese peroxidase was excreted into the medium after five to seven days. Depending on the growth conditions, the white rot fungus produces Manganese peroxidase (MnP) to about 80% purity, based on protein concentration. After filtration and concentration of the extracellular fluid, the crude enzyme can be used without further purification. However, proteases that are present in the concentrate could degrade the enzyme and, therefore, decrease the activity during application. To separate the enzymes of interest from proteases, a simple DEAE cellulose column chromatography step gives a 50–70% yield of partially purified, active and stable enzyme.

TABLE 2

TRACE ELEMENTS (PER LITER)

| Amount | Component |
|---|---|
| 1.5 g | nitrilotriacetic acid |
| 3 g | $MgSO_4 \cdot 7H_2O$ |
| 1 g | NaCl |
| 0.1 g | $FeSO_4 \cdot 7H_2O$ |
| 0.1 g | $CoSO_4$ |
| 0.1 g | $CaCl_2 \cdot 2H_2O$ |
| 0.1 g | $ZnSO_4 \cdot 7H_2O$ |
| 0.01 g | $CuSo_4 \cdot 5H_2O$ |
| 0.01 g | $AlK(SO_4)_2 \cdot 12H_2O$ |
| 0.01 g | $H_3BO_3$ |
| 0.01 g | $Na_2MoO_4 \cdot 2H_2O$ |

The crude enzyme concentrate is dialyzed against 10 mM of a suitable equilibration buffer, pH 7.0–8.0, loaded on an appropriate sized column and eluted with a linear NaCl gradient 0→0.5M. MnP elutes at around 0.1M NaCl and LiP (predominantly isozyme $H_2$) at around 0.15M NaCl. The active peak fractions are concentrated by ultrafiltration (Amicon PM30 or equivalent) and stored frozen until use.

The crude Manganese peroxidase is stable for several days at room temperature. In one example, the crude enzyme had lost less that 10% of its activity after 24 hours at 20° C. The stability of the enzyme at 20° C. can be greatly increased by the elimination of contaminating proteases. Enzyme which had been purified by the method above, retained over 93% of its activity after storage at room temperature for 77 days.

EXAMPLE 1

Using the purified enzyme, a number of model organic compounds were screened to determine which could be oxidized by the enzymatically produced Mn(III). Table 3 shows that Mn(III) is the reactive species generated by Manganese peroxidase which is responsible for the oxidation of organics. Note that "+" indicates a positive reaction as measured by disappearance of a peak, marked color change and/or shift in absorbance. Note further that "(+)" indicates a less pronounced positive reaction.

TABLE 3

COMPOUNDS DEGRADED

| Compound | Spectral Changes |
|---|---|
| 2,6-Dimethoxyphenol | + |
| 2,4-Dichlorophenol | + |
| 2,4,6-Trichlorophenol | + |
| Pentachlorophenol | (+) |
| Methoxyphenol (Guaiacol) | + |
| Benzo [a] pyrene | (+) |
| Crystal violet | + |
| Eosine yellowish | + |
| Brilliant blue G | + |
| Brilliant blue R | + |
| Thymol blue | + |
| Bromothymol blue | (+) |
| Bromophenol blue | + |
| Methyl green | + |
| Malachite green | + |
| Amido black | + |
| Xylene cyanole | + |
| Murexide | + |
| Pyronin Y | (+) |
| Phenol red | + |
| p-Cresol | + |
| p-Toluidine | + |
| N,N,N',N'-Tetramethyl-p-phenylenediamine | + |

Some reactions shown in Table 3 are pH-dependent, e.g., 2,4,6-Trichlorophenol reacts fast at pH 3.0 and slow at pH 5.0.

EXAMPLE 2

In this example, the use of Manganese peroxidase and a semi-permeable membrane system is examined to degrade 2,4,6-Trichlorophenol. In the first experiment, a 50 liter starting solution (10 mM Na-lactate, pH 5.0; 0.50 mM $MnSO_4$; 0.25 mM $H_2O_2$) was prepared. Manganese Peroxidase (6,000 units) was added to 4 liters of this start solution to make a reaction solution. A 50 liter treatment solution (50 mM Na-acetate, pH 3.0; 60 ppm (3g) 2,4,6-Trichlorophenol) was employed.

The starting solution was pumped into the reaction solution at a rate of approximately 0.8 liters per minute and the reaction solution was filtered through three cassettes (15 sq. ft.) of Millipore Pellicon 10K MWCO at a rate of 0.8 liters per minute. Thereafter, the flux was added to the treatment solution which was mixed by a diaphragm pump for a faster reaction.

Figure 4A:
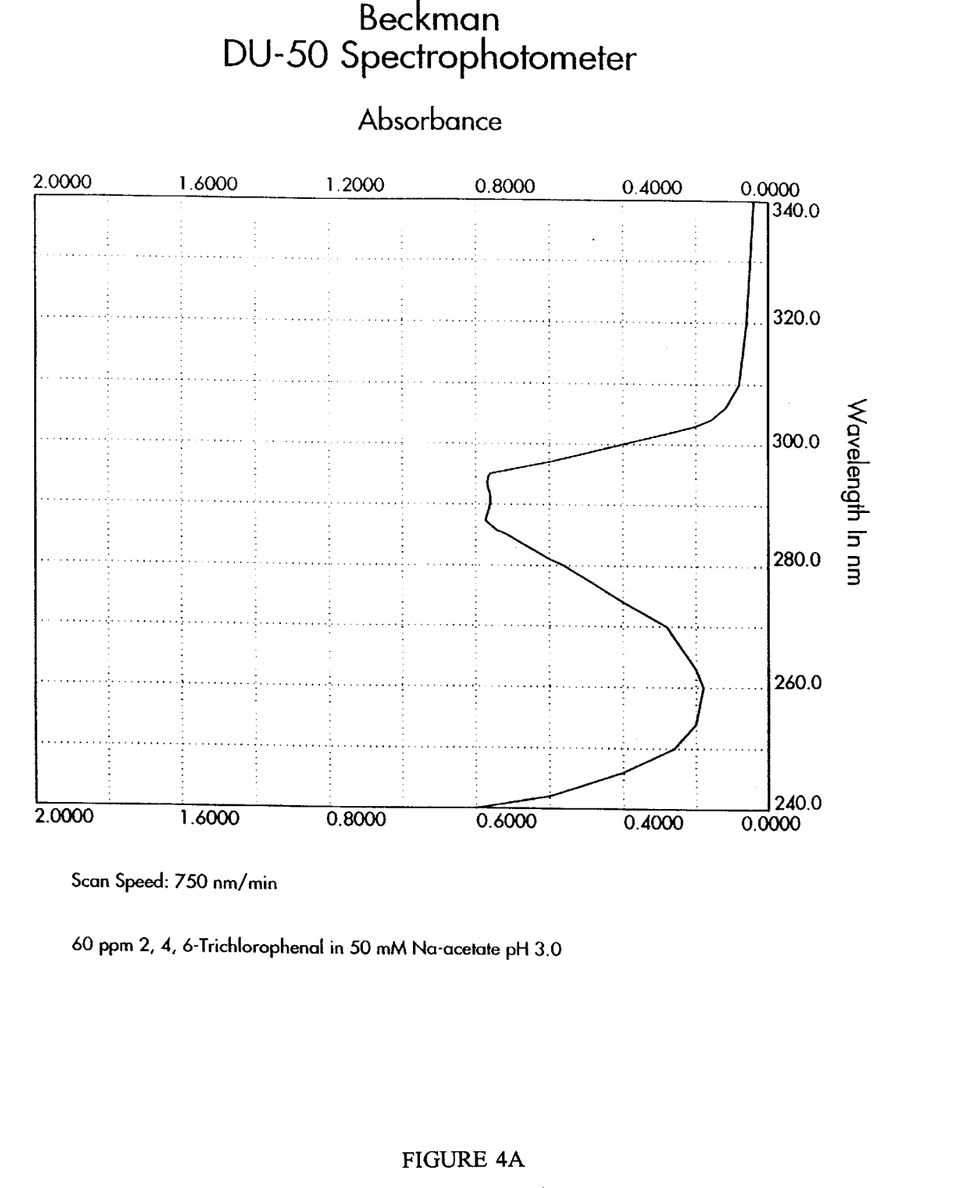
FIG. 4A is a graph showing the absorption spectra of a waste stream.
Figure 4B:
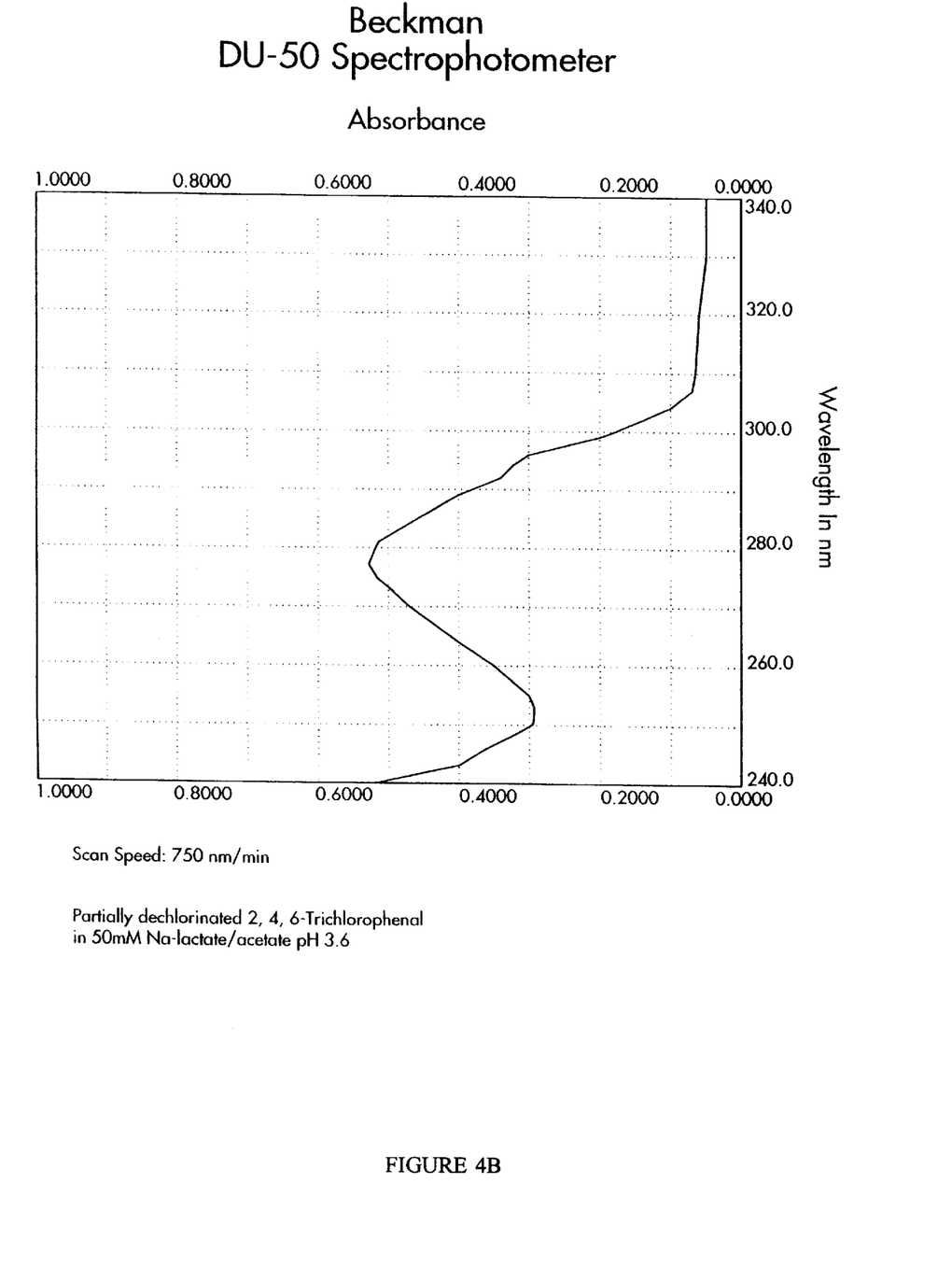
FIG. 4B is a graph showing the absorption spectra of a waste stream following treatment according to one embodiment of the method of the present invention.

When the reaction was monitored by spectral change of the treatment solution, there was only a 25% change (see FIGS. 4A and 4B) ($\Delta A_{274}$ was a factor of 2.6). Measurement of the reaction intermediate indicated that the Mn(III) lactate concentration was 16 to 50% of the expected value. Interestingly, the flow rate was only about 0.5 liters per minute.

From the result, it appeared that the Na-lactate concentration was too low and that Mn(III) precipitated in the reaction solution, resulting in a suspension unable to cross the filtration membrane. This suspension also decreased the flux rate. Clearly, the concentration of lactate, $MnSO_4$, enzyme and $H_2O_2$ have to be balanced to provide the maximum delivery of Mn(III)-lactate to the substrate to be oxidized.

To solve the problem, a new 50 liter start solution (50 mM Na-lactate, pH 5.0; 0.50 mM $MnSO_4$; 0.25 mM $H_2O_2$) was prepared. Manganese Peroxidase (5,400 units) was added to 4 liters of this start solution to make a reaction solution. A new 50 liter treatment solution (50 mM Na-lactate, pH 3.0; 30 ppm (1.5 g) 2,4,6-Trichloro-phenol) was employed.

The solutions were pumped and filtered as before except that the treatment solution was equipped with a pH probe to adjust the pH to below 4.0. During the experiment, the pH did not rise above 3.4.

Figure 5A:
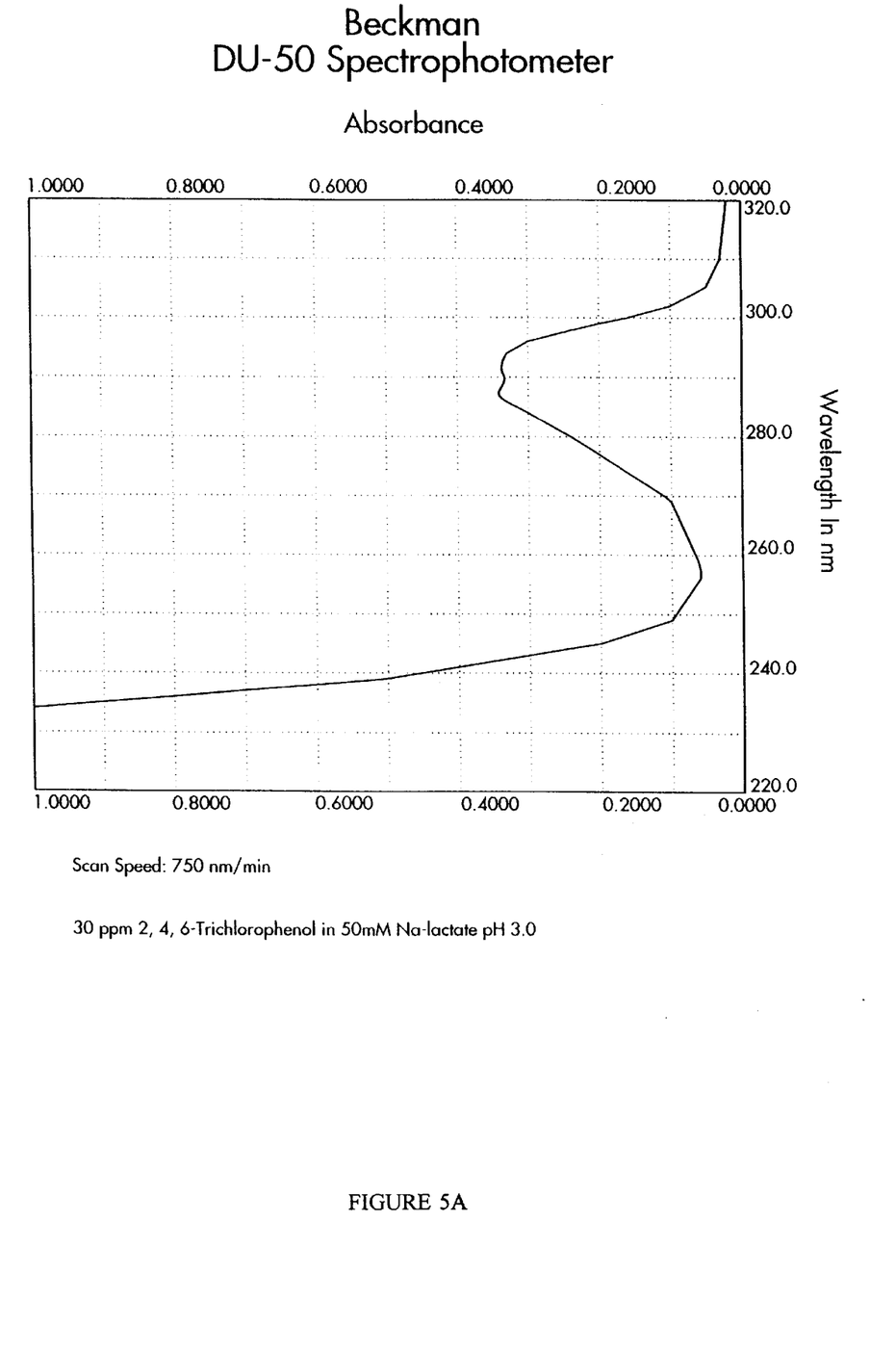
FIG. 5A is a graph showing the absorption spectra of a waste stream.
Figure 5B:
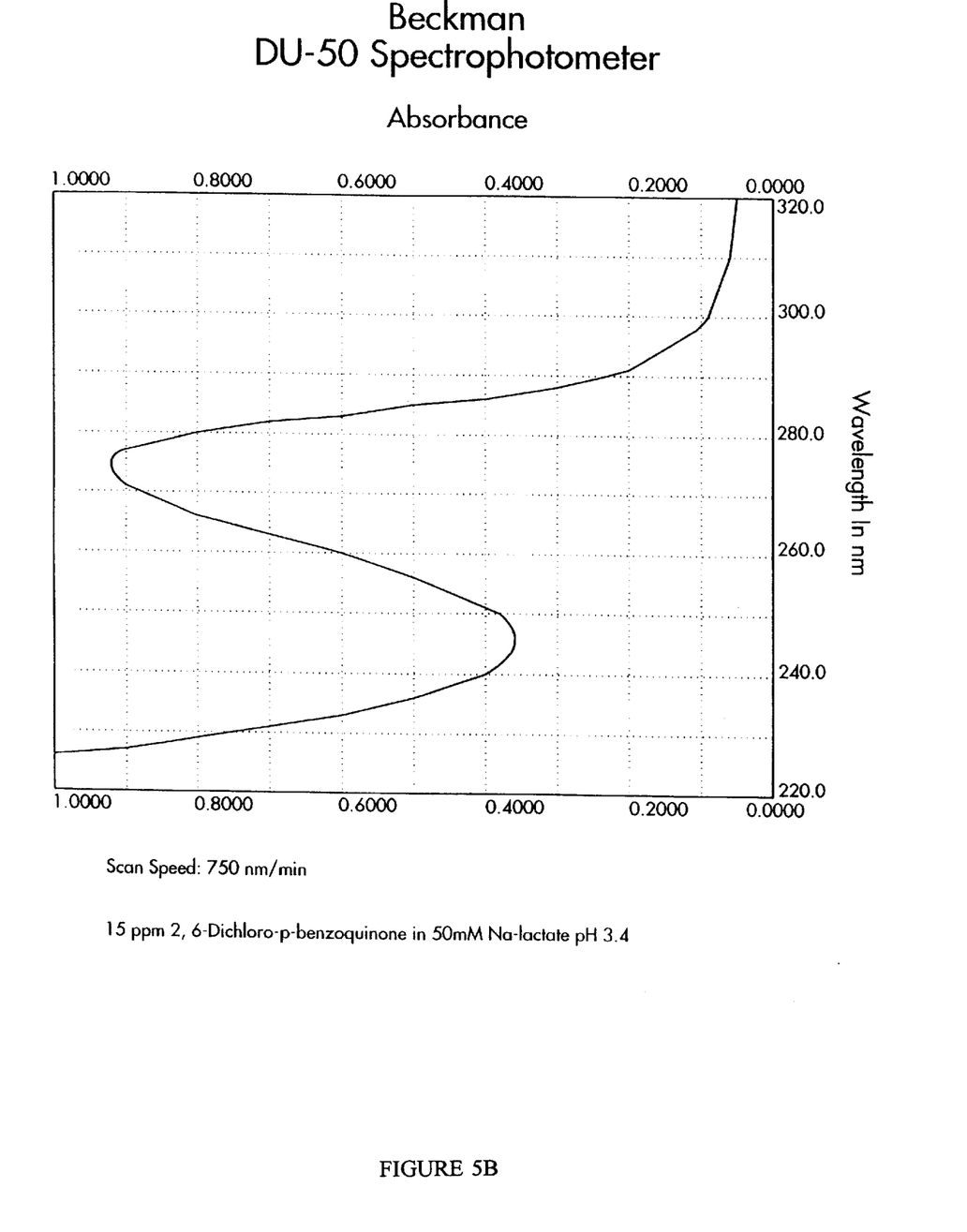
FIG. 5B is a graph showing the absorption spectra of a waste stream following treatment according to a preferred embodiment of the method of the present invention.

When the reaction was monitored by spectral change of the treatment solution, there was approximately a 100% change (see FIGS. 5A and 5B) ($\Delta A_{274}$ was a factor of 11.5). Measurement of the reaction intermediate indicated that the Mn(III) lactate concentration was 84–100% of the expected value. The flow rate was a satisfactory 0.7 liters per minute.

EXAMPLE 3

In this example, the impact of membrane size on flux rate was demonstrated. Three membranes were employed: 1) an Amicon PM 10 with a 10,000 MW cut-off; 2) an Amicon PM 30 with a MW cut-off of 30,000 Daltons; and 3) an Amicon YM 30 with a MW cut-off of 30,000 Daltons and having low protein binding characteristics. A 100 ml starting solution was prepared (25 mM Na-lactate, pH 5.0; 1 mM $MnSO_4$; 0.5 mM $H_2O_2$) Manganese Peroxidase (1.5 units per ml) was added and pressure was applied to the reaction mix. The flux was collected and the time was recorded (see Table 4).

TABLE 4

| Membrane | Pressure | Flux (ml) | Time (Min) | Ml/Min | % of 1 |
| --- | --- | --- | --- | --- | --- |
| A |  |  |  |  |  |
| 1) | 36 psi | 91 | 17 | 5.35 | 100 |
| 2) | 36 psi | 93 | 12 | 7.75 | 145 |
| 3) | 36 psi | 89 | 11 | 8.09 | 150 |
| B |  |  |  |  |  |
| 1) | 36 psi | 400 | 78 | 5.13 | 100 |
| 2) | 36 psi | 400 | 53 | 7.55 | 147 |
| 3) | 36 psi | 400 | 61 | 7.84 | 153 |

Note that the 30,000 Mw membranes clearly show a better flux rate than the published 10,000 MW membranes.

What is claimed is:

1. A method of degrading compounds contained in a liquid or solid waste stream, comprising the steps of:
   a) providing in any order i) a reaction containing means having a semi-permeable membrane partition and first and second sides of said partition, ii) a manganese peroxidase derived from a white rot fungus, for which said membrane is not permeable, and iii) at least one substrate for said peroxidase;
   b) adding in any order, under conditions suitable and for a time sufficient to produce a reaction intermediate that is capable of degrading compounds in said waste stream, i) to said first side of said partition, said peroxidase and said substrate to create a reaction mixture, thereby generating a reaction intermediate for which said membrane is permeable, ii) to said second side of said partition, said compound-containing waste stream; and
   c) applying a pressure to said reaction mixture on said first side of said partition so as to force said reaction intermediate across said membrane into said compound-containing waste stream, under conditions suitable and for a time sufficient to degrade said compounds by the action of said intermediate upon said compounds, thereby degrading said compounds.

2. The method of claim 1 wherein said fungus is selected from the group consisting of *Phanerochaete chrysosporium, Dichromitus squalens, Phlebia radiata, Lentinula edodes, Trametes versicolor, Coriolopsis occidentalis,* and *Rigidoporus lignosus*.

3. The method of claim 1 wherein said substrate is Mn(II).

4. The method of claim 3 wherein said Mn(II) is added in the presence of an α-hydroxy acid and hydrogen peroxide.

5. The method of claim 4 wherein said reaction intermediate is a Mn(III)-α-hydroxy acid complex.

6. The method of claim 5 wherein said α-hydroxy acid is selected from the group consisting of lactic, malonic, malic, oxalic, pyruvic and tartaric acid.

7. A method of degrading compounds contained in a liquid or solid waste stream, comprising the steps of:
   a) providing in any order i) a first reaction containing means having a semi-permeable membrane partition and first and second sides of said partition, ii) a manganese peroxidase derived from a white rot fungus, for which said membrane is not permeable, iii) at least one substrate for said enzyme, and iv) a second reaction containing means containing a waste stream;
   b) adding to said first side of said partition of said first reaction containing means, under conditions suitable and for a time sufficient to produce a reaction intermediate that is capable of degrading compounds in said waste stream, said peroxidase and said substrate to create a reaction mixture, thereby generating a reaction intermediate for which said membrane is permeable;
   c) applying a pressure to said reaction mixture on said first side of said partition so as to force said reaction intermediate across said membrane and so as to collect the reaction intermediate on said second side of the partition; and
   d) adding said reaction intermediate to said second reaction containing means wherein said waste stream is contained and under conditions suitable and for a time sufficient to degrade said compounds by the action of said intermediate upon said compounds, thereby degrading the compounds.

8. The method of claim 7 wherein said adding of said reaction intermediate in step (d) comprises pumping said intermediate from said first reaction containing means to said second reaction containing means.

9. The method of claim 7 wherein said fungus is selected from the group consisting of *Phanerochaete chrysosporium, Dichromitus squalens, Phlebia radiata, Lentinula edodes, Trametes versicolor, Coriolopsis occidentalis,* and *Rigidoporus lignosus*.

10. The method of claim 7 wherein said substrate is Mn(II).

11. The method of claim 10 wherein said Mn(II) is added in the presence of an α-hydroxy acid.

12. The method of claim 11 wherein said reaction intermediate is a Mn(III)-α-hydroxy acid complex.

13. The method of claim 12 wherein said α-hydroxy acid is selected from the group consisting of lactic, malonic, malic, oxalic, pyruvic and tartaric acid.

14. A method of degrading halogenated aromatic compounds contained in a liquid or solid waste stream, comprising the steps of:
   a) providing in any order i) a reaction containing means having a semi-permeable membrane partition and first and second sides of said partition, ii) manganese peroxidase derived from *Phanerochaete chrysosporium,* for which said membrane is not permeable, and iii) substrate for said peroxidase;
   b) adding in any order under conditions suitable and for a time sufficient to produce a reaction intermediate that is capable of degrading halogenated aromatic compounds in said waste stream i) to said first side of said partition said peroxidase and said substrate to create a reaction mixture, thereby generating a reaction intermediate for which said membrane is permeable, ii) to said second side of said partition, said compound-containing waste stream; and c) applying a pressure to said reaction mixture on said first side of said partition, so as to force said reaction intermediate across said membrane into said compound-containing waste stream under conditions suitable and for a time sufficient to degrade said halogenated aromatic compounds by the action of said intermediate upon said compounds, thereby degrading said halogenated aromatic compounds.

15. The method of claim 14 wherein said substrate is Mn(II).

16. The method of claim 15 wherein said Mn(II) is added in the presence of an α-hydroxy acid and hydrogen peroxide.

17. The method of claim 14 wherein said reaction intermediate is a Mn(III)-α-hydroxy acid complex.

18. The method of claim 16 wherein said α-hydroxy acid is selected from the group consisting of lactic, malonic, malic, oxalic, pyruvic and tartaric acid.

19. The method of claim 14, wherein said halogenated aromatic compounds comprise halogenated lignins.

20. The method of claim 19, wherein said halogenated lignin is chlorolignin.

21. A method of degrading halogenated aromatic compounds contained in a liquid or solid waste stream, comprising the steps of:

a) providing in any order i) a reaction containing means having a semi-permeable membrane partition and first and second sides of said partition, ii) manganese peroxidase derived from *Phanerochaete chrysosporium*, for which said membrane is not permeable, iii) Mn (II) substrate for said peroxidase, and iv) a-hydroxy acid and hydrogen peroxide;

b) adding in any order under conditions suitable and for a time sufficient to produce a reaction intermediate that is capable of degrading halogenated aromatic compounds in said waste stream i) to said first side of said partition, said peroxidase, said Mn (II) substrate, said a-hydroxy acid, and said hydrogen peroxide to create a reaction mixture, thereby generating a reaction intermediate for which said membrane is permeable, ii) to said second side of said partition, said compound-containing waste stream; and c) applying a pressure to said reaction mixture on said first side of said partition so as to force said reaction intermediate across said membrane into said compound-containing waste stream under conditions suitable and for a time sufficient to degrade said halogenated aromatic compounds by the action of said intermediate upon said compounds, thereby degrading said halogenated aromatic compounds.

22. The method of claim 21 wherein said reaction intermediate is a Mn(III)-α-hydroxy acid complex.

23. The method of claim 21 wherein said α-hydroxy acid is selected from the group consisting of lactic, malonic, malic, oxalic, pyruvic and tartaric acid.

24. A method of degrading halogenated aromatic compounds contained in a liquid or solid waste stream, comprising the steps of:

a) providing in any order i) a reaction containing means having a semi-permeable membrane partition and first and second sides of said partition, ii) manganese peroxidase derived from *Phanerochaete chrysosporium*, for which said membrane is not permeable, iii) Mn (II) substrate for said peroxidase, and iv) a-hydroxy acid and hydrogen peroxide;

b) adding in any order under conditions suitable and for a time sufficient to produce a Mn(III)-a-hydroxy acid complex that is capable of degrading halogenated aromatic compounds in said waste stream i) to said first side of said partition, said peroxidase, said Mn (II) substrate, said a-hydroxy acid, and said hydrogen peroxide, thereby generating a Mn(III)-a-hydroxy acid complex for which said membrane is permeable, ii) to said second side of said partition, said compound-containing waste stream; and c) applying a pressure to said reaction mixture on said first side of said partition so as to force said Mn(III)-a-hydroxy acid complex across said membrane into said compound-containing waste stream under conditions suitable and for a time sufficient to degrade said halogenated aromatic compounds by the action of said complex upon said compounds, thereby degrading said halogenated aromatic compounds.

25. The method of claim 24 wherein said α-hydroxy acid is selected from the group consisting of lactic, malonic, malic, oxalic, pyruvic and tartaric acid.

* * * * *